United States Patent
Hoppe et al.

(10) Patent No.: US 9,878,108 B2
(45) Date of Patent: Jan. 30, 2018

(54) SYRINGE BODY/NEEDLE ASSEMBLY

(71) Applicant: SCHOTT AG, Mainz (DE)

(72) Inventors: Bernd Hoppe, Ingelheim (DE); Daniela Seiler, Alezey (DE); Andreas Roters, Mainz (DE); Kathrin Schellenberg, Hochheim (DE)

(73) Assignee: SCHOTT AG, Mainz (DE)

(*) Notice: Subject to any disclaimer, the term of this patent is extended or adjusted under 35 U.S.C. 154(b) by 149 days.

(21) Appl. No.: 14/633,171

(22) Filed: Feb. 27, 2015

(65) Prior Publication Data

US 2015/0165134 A1    Jun. 18, 2015

Related U.S. Application Data

(62) Division of application No. 13/822,438, filed as application No. PCT/EP2011/004364 on Aug. 30, 2011, now Pat. No. 8,998,853.

(30) Foreign Application Priority Data

Sep. 13, 2010 (DE) .................. 10 2010 045 095

(51) Int. Cl.
    *A61M 5/34* (2006.01)
(52) U.S. Cl.
    CPC .............. *A61M 5/343* (2013.01); *A61M 5/34* (2013.01); *A61M 5/349* (2013.01); *A61M 2205/0211* (2013.01)
(58) Field of Classification Search
    CPC ......... A61M 5/343; A61M 5/34; A61M 5/349
    See application file for complete search history.

(56) References Cited

U.S. PATENT DOCUMENTS

| | | | |
|---|---|---|---|
| 3,194,784 A | 7/1965 | Bowen | |
| 3,364,002 A | 1/1968 | Michel | |
| 3,390,678 A | 7/1968 | Bradley et al. | |
| 2002/0138042 A1 | 9/2002 | Llorach et al. | |

(Continued)

FOREIGN PATENT DOCUMENTS

| | | |
|---|---|---|
| EP | 2025357 A1 | 2/2009 |
| WO | 02066387 A1 | 8/2002 |
| WO | 2006136364 A1 | 12/2006 |

OTHER PUBLICATIONS

English Translation of International Search Report dated Jun. 21, 2012 corresponding to International Patent Application No. PCT/EP2011/004364, 3 pages.

(Continued)

*Primary Examiner* — Bradley Osinski
(74) *Attorney, Agent, or Firm* — Ohlandt, Greeley, Ruggiero & Perle, L.L.P.

(57) ABSTRACT

A syringe body/needle assembly is provided that is free of an organic adhesive bond. The assembly includes a syringe body having a nozzle that has an opening; a needle fixed in the syringe body or in the nozzle; and a connecting body made of doped glass. The opening through which the needle is introduced into an interior of the syringe body is hermetically sealed to the needle. The connecting body includes a first material that absorbs more electromagnetic radiation within a wavelength range than a second material from which the syringe body is made.

19 Claims, 6 Drawing Sheets

(56) References Cited

U.S. PATENT DOCUMENTS

2008/0099470 A1* 5/2008 Von Bulow ........... A61M 5/343
219/678
2009/0043266 A1* 2/2009 Heidl .................... A61M 5/343
604/240

OTHER PUBLICATIONS

Written Opinion of the International Searching Authority dated Jun. 21, 2012 corresponding to International Patent Application No. PCT/EP2011/004364, 5 pages.
English Translation of International Preliminary Report on Patentability dated Mar. 14, 2013 corresponding to International Patent Application No. PCT/EP2011/004364, 6 pages.
European Patent Office Office Action dated Nov. 3, 2014 in corresponding European Application No. 11 754 296.9 with machine translation, 6 pages.

* cited by examiner

SYRINGE BODY/NEEDLE ASSEMBLY

CROSS REFERENCE TO RELATED APPLICATIONS

This application is a divisional of Application Serial No. 13/822,438 filed Mar. 12, 2013that issued as U.S. Pat. No. 8,998,853 on Apr. 7, 2015, which is a National Stage Application of International Application No. PCT/EP2011/004364 filed Aug. 30, 2011, which claims benefit under 35 U.S.C. §119(a) of German Patent Application No. 10 2010 045 095.2 filed Sep. 13, 2010, the entire contents of all of which are incorporated herein by reference.

BACKGROUND

1. Field of the Disclosure

The invention relates to a syringe body/needle assembly that avoids the use of organic adhesives for bonding syringe body and needle.

2. Description of Related Art

For manufacturing syringes, e.g. for pharmaceutical applications, the actual syringe body is usually formed from a glass tube using multistage hot forming processes. The syringe body as formed is then inspected and subsequently cooled in a lehr.

Syringe systems that are delivered filled with the drug to be administered, often have the needle already integrated. To this end, the needle may be glued into the syringe nozzle (also known as syringe cone) after the syringe body has been formed. The syringe cone may have any, not necessarily convergent shape. Below, a syringe cone refers to any nozzles having cross section shapes whose function is to reduce the fluid-carrying cross section compared with the plunger's diameter.

The needle is first introduced to the intended position in the nozzle, and is then fixed using a liquid organic adhesive which is added at room temperature and is cured, for example under ultraviolet light. Thereafter, the so prepared syringe body/needle assembly is cleaned, the inner wall of the syringe body is siliconized, and a cap is placed on the needle and nozzle. Then, this syringe system assembly is sterilized.

Filling of the syringe is then accomplished in the pharmaceutical companies which also place the final stopper with the plunger, for example for injection of the drug, and make the individual packaging.

During the storage period of the prefilled syringe, the drug is continuously in contact with the organic adhesive which fixes the needle in the syringe nozzle. Due to this direct contact between drug and adhesive, components of the adhesive may unintentionally diffuse into the drug and interactions between the drug and components of the adhesive may result. These effects may even be amplified by insufficiently hardened adhesives.

Moreover, when bonding the needle, adhesive might be introduced into the needle. This is particularly problematic when for example a UV-curable adhesive is used. The adhesive introduced into the needle is shielded from the incident UV light by the metallic needle and therefore will not cure, or at least not sufficiently. Uncured adhesive components may then interact with the introduced drug.

Especially proteins, but also DNA and/or RNA complexes can be very sensitive to the slightest contamination. Such contamination may cause conformational changes which then may considerably reduce the effect of the drugs or even eliminate it completely. Since in the modern pharmaceutical industry, more and more of such sensitive drugs are developed, produced and applied, the reduction of possible sources of contamination is becoming increasingly important.

In addition, both the process of siliconizing and the sterilization processes usually involve elevated temperatures. Since these processes are carried out after the needle has been bonded in the syringe body, the variety of possible methods that may be used for these processes is limited by the temperature resistance of the adhesive. Commercially available adhesives today exhibit a maximum temperature resistance of up to 150° C. But in order to be able to provide 100% pyrogen-free packing materials, a baked-on siliconization above 300° C. is required. However, many commercially available UV-curable adhesives lose their strength at these temperatures.

Fixation of needles in pharmaceutical syringes by means of an organic adhesive is described, for example, in documents U.S. Pat. No. 3,194,784 and U.S. Pat. No. 3,390,678.

Besides the use of organic adhesives, however, other methods for fixing the needle in or on the syringe body are known. For example, patent document U.S. Pat. No. 3,364,002 describes a method wherein a needle holder is directly introduced into fused glass of a syringe and so a fused bond is produced. In this case, however, the needle holder is heated to very high temperatures which may lead to a damage of the metal, for example by corrosion.

SUMMARY

Therefore, an object of the invention is to provide a cost efficient method that permits to produce a syringe body/needle assembly in which an adhesive bond by means of organic adhesive is dispensed with.

Another object of the invention is to provide a method for producing a syringe body/needle assembly which exclusively uses inorganic materials in areas that come into contact with filled-in drugs.

Another object of the invention is to provide a syringe body/needle assembly that meets the objectives mentioned above.

Accordingly, a method of the invention for producing a syringe body/needle assembly comprises at least the steps of:
  providing a needle (20) and a syringe body (10) having a nozzle (11), wherein a first material which is provided in the region of the nozzle (11) absorbs more electromagnetic radiation (41) than a second material of the rest of the syringe body (10);
  positioning at least the syringe body (10) and the needle (20) in a relationship for bonding the needle (20) with the syringe body (10) so that in bonded state a hermetically sealed bond is provided between the syringe body (10) and the needle (20);
  producing the bond between the syringe body (10) and the needle (20) by irradiating the first material in the region of the nozzle (11) at least locally by electromagnetic radiation (41) and thereby causing the first material to melt at least partially and to hermetically sealingly fix the needle (20) in the syringe body (10);
  cooling the syringe body/needle assembly (1).

According to a preferred embodiment, the first material in the region of the nozzle absorbs more electromagnetic energy than the second material of the rest of the syringe body. For example, in the wavelength range of the radiation source used the total energy absorption of the first material in the region of the nozzle in a single pass of the radiation is at least absolutely 10% higher, preferably at least absolutely 30% higher, and more preferably at least absolutely 50% higher than that of the second material of the rest of the syringe body. The nozzle of the syringe body may typically be conical; however, generally, other shapes are also included.

In contrast to conventional methods or methods in which heating of the material occurs by an absorption of radiation in the surface zone of the material, the invention is characterized in that heating occurs from the inside outwards, due to the more strongly absorbing first material preferably arranged in the channel of the nozzle, or cone. That is, the inside of the channel is heated faster than the outside of the nozzle, although the radiation passes through the material of the syringe body. In other words, a temperature gradient from the inside outwards results.

According to one embodiment of the invention, the increased radiation absorption may be achieved by a chemical or structural modification of the surface of, for instance, the nozzle. For example, using a suitable surface treatment such as ion exchange, ions may diffuse into the surface of the inner channel of the nozzle, so that radiation absorption is locally increased in the ion diffusion region. Similarly, a surface modification may be achieved by roughening, such as by sand blasting or etching. A coating with a suitable more strongly absorbing material is also conceivable. In these ways, the inner surface of the syringe body nozzle may also be treated, and thus additional connecting material may entirely be dispensed with.

Moreover, the scope of the invention also includes a syringe body with needle, comprising at least one syringe body with a nozzle that has an opening, and a needle. This syringe body with needle may be or may have been produced with the method described above. The needle is fixed in the syringe body, and the opening through which the needle is in communication with the interior of the syringe body is hermetically sealed to the needle. The region of the nozzle includes a first material that absorbs more electromagnetic radiation than the second material from which the rest of the syringe body is made of. The needle is fused into the first material which absorbs more electromagnetic radiation. For example, in the wavelength range of the radiation source used, the total energy absorption of the first material in the region of the nozzle in a single pass of the radiation is at least absolutely 10% higher, preferably at least absolutely 30% higher, and most preferably at least absolutely 50% higher than that of the second material of the rest of the syringe body.

The first material in the region of the nozzle may comprise a connecting body which is arranged in the nozzle. The connecting body comprises a material which absorbs more electromagnetic radiation than the second material of the syringe body.

In order to avoid unnecessary repetition, the features described below refer both to the method and to the product, as far as reasonable and not otherwise stated.

The method of the invention is cost efficient and allows to connect a needle with a syringe body, preferably by exclusively using inorganic material, in particular by means of glass. According to a preferred embodiment of the invention, this method, for instance, also prevents residual stresses from developing in a glass syringe body.

However, the invention is likewise applicable to plastic materials as materials of the syringe body and/or of the connecting body. A particularly preferred material for syringes from plastic material is COC (cyclo-olefin copolymer). According to a first variation of the embodiment of the invention that uses plastic materials, preferably COC, plastic material is used for both the syringe body and the connecting body. According to a second variation, a syringe body of glass is used, but a connecting body of plastic material is employed to connect the needle with the syringe body. Optionally it is not necessary to incorporate radiation absorbing substances into the connecting body, if in the first variation different plastic materials are used which have different spectral absorption characteristics, or if in the second variation the spectral absorption characteristics of glass and plastic material are sufficiently different and an appropriate spectral range is selected for the incident radiation, in which the absorption in the connecting body is higher than in the material of the syringe body. A common feature of the variations of the more general embodiment of the invention that uses plastic materials is that a connection body of plastic material is used, while the syringe body may be made of glass or of plastic material.

The syringe body may preferably comprise an integral nozzle, i.e. molded contiguous to the syringe body, which for example may have the form of a peripheral necking of the syringe body. According to a particularly preferred embodiment of the invention, the connecting body which fixes the syringe cannula or needle to the syringe body may be fused into or to this nozzle.

According to another advantageous embodiment of the invention, glass is used as a material for the syringe body and/or for the at least one connecting body. Especially when using a syringe body and a connecting body made of glass, organic components can then be completely omitted for fixing the needle in the syringe.

In this case, the at least one connecting body may comprise a glass capillary portion and/or a sintered body made of glass and/or glass powder and/or glass paste. Glass paste, herein, refers to glass powder bound with a liquid.

In particular, the first material of the connecting body is chemically and/or structurally different from the second material of the syringe body.

Advantageously, the connecting body may for example comprise doped glass, in particular glass doped with a component that absorbs the radiation used for heating. In this way, it is for example possible to use glass of almost the same composition for the syringe body and the connecting body and still ensure that the first material of the connecting body absorbs more electromagnetic energy than the second material of the syringe body. Particularly advantageously, the connecting body may be doped with compounds of chromium, nickel, copper, iron, cobalt, rare earths (e.g. ytterbium, dysprosium) or with other elements, materials or compounds absorbing in the wavelength range of interest. Combinations of the aforementioned compounds are likewise possible. But it is also possible to use a sintered body of glass as a connecting body, and to add a material to the glass starting powder, which increases absorption of electromagnetic radiation. For example, the glass powder for such a sintered body may be mixed with an absorbent pigment. In this way it is possible to add even such absorbing compounds to the starting powder of the sintered body, which would otherwise in the glass melting process be subject to significant changes and would lose essential properties. It is also possible to introduce the above mentioned glass dopants in this process step. An advantage thereof is that the same material may be used as a starting powder for the connecting body as well as for the rest of the syringe body.

According to a preferred embodiment of the invention, a preferably annular inorganic connecting body or bonding body is inserted between the needle and the nozzle wall of a syringe body. This connecting body may be heated locally and fused, due to increased absorption of high-energy electromagnetic radiation, so that the needle is hermetically sealingly bonded to the nozzle. It goes without saying that the hermetic sealing between needle and syringe body does not refer to the needle itself which indeed should continue to be functional. That means that despite of the hermetic sealing between the needle and the syringe body, the needle is of course suitable for injecting the drug later to be filled into the syringe.

Electromagnetic radiation in the sense of the invention refers to any electromagnetic radiation that causes heating up to the required bonding temperature of the first material in the region of the nozzle, for example of a connecting body. Particularly preferably, however, it refers to electromagnetic radiation that is not or only very little absorbed by the second material of the syringe body, but good or very good by the first material in the region of the nozzle.

Especially preferably, irradiation is accomplished using electromagnetic radiation from one or more UV radiation sources, and/or radiation sources emitting in the visible range, and/or infrared radiation sources, in particular infrared radiation sources emitting short wave infrared radiation, and/or microwave radiation sources.

For example, mercury vapor lamps may be used as a UV radiation source. Xenon short arc high pressure lamps may be used as a radiation source that emits in the visible range. Lasers such as Nd:YAG lasers, or thermal radiators such as tungsten-IR radiators are suitable as infrared radiation sources. Microwave radiation sources that may be used in conjunction with the invention include for example magnetrons.

Most preferably, for example for neutral uncolored glasses, short wave infrared radiation (SWIR radiation) is used, in particular in a range around 1 μm. Preferred wavelengths of the employed SWIR radiation range from 800 to 3000 nanometers, more preferably from 800 to 1500 nanometers. Such electromagnetic radiation may for example be generated using a tungsten-halogen IR radiator which may have a color temperature from 1500 K to 3500 K.

When using such a heating technology, the heating is not only determined by the temperature of the oven, but substantially by the IR radiation from the heating elements and the absorption behavior of the body to be heated. By carefully selecting and adjusting the radiation and absorption ratios, glass, such as a highly shortwave infrared radiation absorbing connecting body in the nozzle of the poorly radiation absorbing syringe body, can be locally heated and selectively fused, at least partially.

Differences in the resulting radiation absorbance between the connecting body and the syringe body may be achieved, for example, by using different types of glass, by doping with coloring elements, or by structural differences, such as by introducing scattering centers or using sintered bodies.

Especially preferably, the step of producing the bond between the syringe body and the needle comprises fusing the at least one connecting body, at least partially. The fused first material of the connecting body, after having been cooled, engages the wall of the syringe body and fits around the needle so that the needle is fitted into the syringe body by a hermetically sealing bond.

When using connecting bodies, glass tube sections as well as sintered glass tubes may be used according to a preferred embodiment. However, bonding between needle and syringe body may also be accomplished by locally melting glass powder or a glass paste.

According to one embodiment of the invention, the connecting body which connects the syringe body and the needle is disposed in or on the nozzle of the syringe body. According to preferred embodiments of the invention, it is suggested to place the connecting body at the upper or at the lower end of the nozzle. However, a central arrangement thereof is likewise possible. The nozzle may be filled completely or partially by the connecting body. Also, the connecting body may be placed on the proximal or distal end of the nozzle. In other words, this means that in its proximal arrangement the connecting body is placed on the nozzle from the interior of the syringe body. In its distal arrangement, the connecting body is arranged at the free end of the nozzle, i.e. opposite the actual syringe body.

According to another preferred embodiment of the invention, not only one connecting body is used to fix the needle in the syringe body, but more than one. For example, the needle may be fused into the nozzle using two connecting bodies, e.g. in the upper and lower regions of the nozzle.

Also, advantageously, the nozzle of the syringe body may have recesses into which the connecting body may be fitted. On the one hand this facilitates the arrangement of the syringe body, connecting body and needle before actually connecting these elements. On the other hand, the bond in the final syringe body/needle assembly may be stabilized, since the recess acts as an abutment relative to the pressure exerted on the connecting body when administering an injection. This is the case if the recess opens in the proximal direction, i.e. towards the syringe body. It is of course also possible to provide a recess which opens in the distal direction, i.e. towards the free end of the nozzle.

Besides the local input of electromagnetic energy especially into the connecting body which is to connect the syringe body and the needle, at least the syringe body may also be heated. In particular, the syringe body may be heated to a temperature at which the material thereof, or the second material, at least reaches its strain point. When using glass the strain point is at a viscosity of $\eta=10^{14.5}$ dPa·s. At such a viscosity, the glass of the syringe body is still dimensionally stable, while it is able to relax stresses that may arise due to the use of materials having different thermal expansion coefficients.

The additional heating of at least the syringe body may be accomplished using infrared radiation and/or a hot air stream, for example. Generally, various conventional heaters may be employed to this end. Especially preferably, the syringe body is heated simultaneously with the heating of the connecting body using the same radiation source. For example, the difference in absorbance of the syringe body and the connecting body is selected such that the connecting body reaches the bonding temperature and the syringe body reaches the strain point.

Particularly preferably, the step of establishing the connection between the syringe body and the needle may be followed by a thermal post-treatment. This thermal post-treatment during which the syringe body/needle assembly is reheated, in particular to at least the strain point temperature, advantageously relaxes any residual stresses, at least in the syringe body, that might still exist and have been induced by different thermal expansion coefficients of the materials, and/or by differently heated areas of the syringe body and the needle.

If a $CO_2$ laser is used as a radiation source, which is the case in prior art, which laser naturally emits in a wavelength range around 10 μm, the radiation will be absorbed directly at the surface of the syringe body and will not preferably heat the connecting body. Further disadvantages such as complex and expensive beam guidance, risk of rapid overheating of the surface of the syringe nozzle, excessive residual stresses in the bonded syringe body, and time-consuming processes due single-part treatment are avoided by the technology presently disclosed.

Moreover, by the selective local heating of the connecting body the steel needle may be prevented from overheating. Moreover, by adjusting the radiation absorbance of the connecting body, it is possible to optimize the processing time such that in case of any critical temperature increase of the metal needle to be bonded, the latter will not suffer impermissible damage. Furthermore, corrosion of the metal of the needle can be reduced or completely avoided in particular by additionally using nitrogen or other inert gases in the region of the needle.

Surprisingly, in bonding experiment that were carried our it has been found that stress cracks do no occur, especially not in the bonded area, but neither in the rest of the syringe body. This had initially been classified as impossible, since the expansion coefficients of the metal needle ($10-20\times10^{-6}$/K), and of the glass of the connecting body or of the syringe body ($0-5\times10^{-6}$/K) are considerably far apart. It had been assumed that tensions would inevitably occur. However, measurements on bonded syringe bodies have shown that the residual stresses are well below the critical permissible crack tensions allowable for the syringe body. It could be demonstrated by the experiments that the large differences in the coefficients of expansion of glass and metal do not necessarily result in excessive residual stresses, because the local temperature control permits to adjust low residual stresses in an appropriate way. Differences in the expansion coefficients in particular lead to residual stresses where temperature is locally homogeneous. If, as in the case presently described, the temperature is locally inhomogeneous, temperature-induced changes in length may compensate and thus result in reduced residual stresses.

When producing the syringe body from glass, usually tungsten-containing pins are used to form the narrow nozzle channel, in particular pins of tungsten metal. Thereby, traces of tungsten may be deposited in the nozzle channel during the hot forming step. With sensitive drugs, tungsten may lead to undesirable interactions with the drugs, which reduce the effect of the drug. If, in contrast, a connecting body according to the invention is used, the nozzle channel may generally be enlarged. With such comparatively large nozzle channels, the use of tungsten metal in form of molding tools is no longer necessary, so that these unwanted interactions can be avoided.

BRIEF DESCRIPTION OF THE DRAWINGS

The invention will now be explained with reference to examples and drawings. In the various drawings, the same or similar features are designated with the same reference numerals. In the drawings.

DETAILED DESCRIPTION OF THE INVENTION

Figure 1:
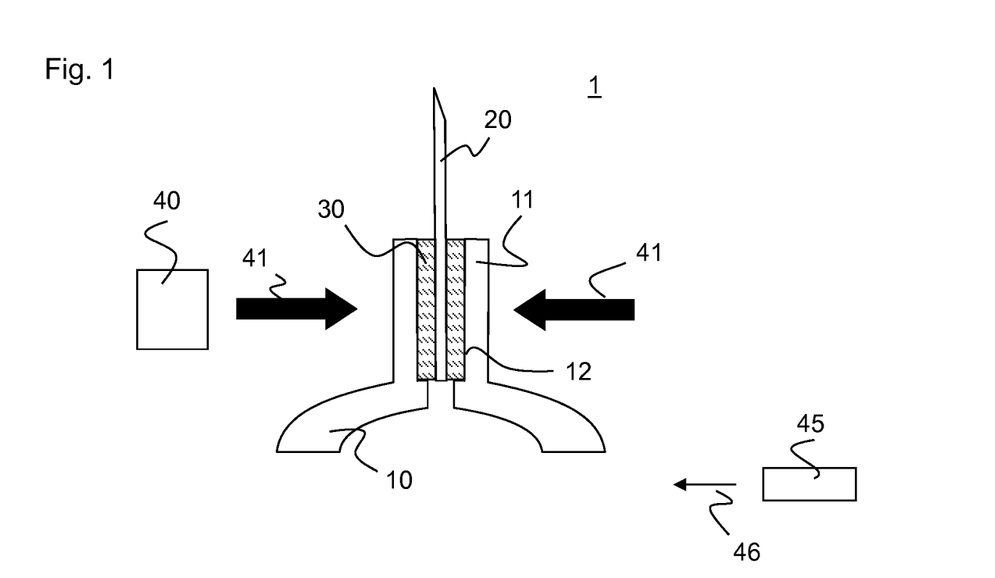
FIG. 1 shows a schematic cross section through a syringe body/needle assembly, for explaining the basic principle of the invention.

FIG. 1 shows the basic structure of an integrated syringe body/needle assembly 1. Syringe body/needle assembly 1 comprises a syringe body 10, a needle 20, and a connecting body 30. Syringe body 10 has a nozzle 11 with a recess 12 into which the connecting body 30 is fitted. Connecting body 30 comprises a first material which absorbs more electromagnetic radiation 41 than syringe body 10, with the syringe body 10 also including nozzle 11.

For producing the syringe body/needle assembly 1, syringe body 10, needle 20 and connecting body 30 are arranged in a relationship to one another as provided in the final assembly. Then, at least part of the surface of the region of connecting body 30 is irradiated by electromagnetic radiation 41 using a device for generating electromagnetic radiation 40. To achieve selective heating of the connecting body 30, the connecting body 30 substantially comprises a material absorbing well the emitted electromagnetic radiation 41. In contrast, syringe body 10 and the associated nozzle 11 comprise a second material which absorbs the emitted electromagnetic radiation 41 as little as possible. Advantageously, electromagnetic radiation 41 passes through the second material of syringe body 10 and nozzle 11 preferably without any or with only little transmission loss. In this way, selective heating of the connecting body 30 can be achieved, so that the latter melts, at least partially. The second material of syringe body 10, by contrast, is preferably heated as little as possible by this irradiation 41. This, inter alia, prevents the syringe body 10 from being deformed during "fusing" of the connecting member 30. Thus, a temperature gradient results which decreases from inside out towards the surface of the nozzle.

Due to the at least partial fusing of the first material of the connecting body 11, needle 20 is fixed in or at the nozzle 11, on the one hand. On the other hand, moreover, the gap or opening between the wall of nozzle 11 and needle 20 is hermetically sealed, as the fused first material of the connecting body 30 engages the nozzle wall 11 and around needle 20 and is bonded thereto.

Preferably, glass may be used as a material for syringe body 10 and/or for the at least one connecting body 30. Further preferably, the at least one connecting body 30 may comprise a glass capillary portion and/or a sintered glass body and/or glass powder and/or glass paste. The good absorption characteristics in contrast to the second material of syringe body 10 can be obtained by using a chemically or structurally different material. Especially preferably, the connecting body 30 comprises doped glass, for example glass doped with chromium, iron or nickel oxide, and/or a sintered body of doped glass, in particular of a glass doped with chromium, iron or nickel oxide, and/or a sintered body of glass whose starting powder was mixed with coloring pigments, for example.

Preferred sources for generating electromagnetic radiation for selectively heating the connecting body 30 include one or more UV radiation sources, for example mercury vapor lamps, and/or radiation sources which emit in the visible range, for example xenon short arc high pressure lamps, and/or infrared radiation sources, in particular infrared radiation sources which emit short wave infrared radiation, such as Nd:YAG lasers, or tungsten IR radiators, and/or microwave radiation sources, such as magnetrons.

According to a particularly preferred embodiment of the invention, however, besides selectively heating the connecting body 30, the syringe body 10 may also be heated by the same radiation source 40. This is advantageous in that stresses which may occur in the nozzle 11 due to the selective heating of the connecting body 30, are mitigated or even largely avoided. In this case, the difference in absorbance of the syringe body and the connecting body is selected, for instance, such that the connecting body reaches the bonding temperature and the syringe body reaches temperatures that prevent excessive residual stresses, for example the strain point temperature, but remains below the softening temperature.

According to another preferred embodiment of the invention, however, in addition to the selective heating of the connecting body 30, the syringe body 10 may be heated by an auxiliary heater 45. This may be advantageous in that stresses which may arise in the nozzle 11 due to the selective heating of the connecting body 30 can be alleviated or even largely prevented.

This auxiliary heater 45 may involve a conventional heating technology. Preferably, additional heating may be accomplished by infrared radiation 46, or by a hot air flow 46.

According to a preferred embodiment of the invention, a syringe body/needle assembly as illustrated in FIGS. 1 through 8 may, for example, be produced as described below.

A syringe body 10 is provided made of glass with the trade name Fiolax® clear having a total length of 45 mm and an outer diameter of 8 mm. Fiolax® clear has a composition, in wt. %, of 75% of $SiO_2$; 10.5% of $B_2O_3$; 7% of $Na_2O_3$; 5% of $Al_2O_3$; 1.5% of CaO, and <1% of BaO. In addition, a needle 20 of stainless steel with the material number 1.4301 according to EN 10088-2 is used, having a total length of 23 mm and an outer diameter of 0.5 mm. Also comprised is a sintered body 30 of Fiolax® clear, doped with 5 wt. % $Fe_2O_3$, having a height of 4 mm, an outer diameter of 1.45 mm, and an inner diameter of 0.55 mm. This system is fixed with the syringe body 10 vertically on a carriage (not shown) and the needle 20 concentrically thereto vertically from above in a needle forceps (not shown) such that the free length of the needle between the top edge of the nozzle 11 and the needle tip is 19 mm. The system is advanced at a speed from 1 cm/s to 10 cm/s through an inline unit 40, which emits short wave IR radiation 41. Within SWIR unit 40 at the height of connecting body 30, in this case sintered body 30, a tungsten halogen IR lamp with a color temperature between 1500 K and 3500 K irradiates nozzle 11 with the sintered body 30 disposed therein or thereon, from the outside. The infrared radiation power is adjusted such that the sintered body 30 fuses within 1 to 120 seconds, preferably within 1 to 60 seconds, and more preferably within 1 to 45 seconds, yet more preferably within 1 to 30 seconds, and most preferably within 1 to 10 seconds to hermetically bond and seal the nozzle 11 to the needle 20. The short fusing time permits to locally limit the heating to the region of the absorbent first material. In this manner, damage to the needle can be prevented, for example.

As an alternative to the example described above with glass as a material of the connecting body and of the syringe body, plastic material may likewise be used for at least one of these elements. A preferred plastic material is COC. The temperatures which are necessary to soften the plastic material are typically much lower than those for glasses.

According to a particularly preferred embodiment of the invention, during the infrared irradiation of the connecting body 30 the entire syringe body 10 and optionally also the needle 20 are heated to several hundred degrees Celsius using a conventional auxiliary heater 45 with, e.g., 500 W of electric power, or an infrared heater, or another suitable heater. The additional heating of the syringe body 10 and optionally of the needle 20 has the effect that excessive stresses due to the local infrared irradiation 41 are prevented from arising in the syringe body 10 or in the nozzle 11.

After the needle 20 has been successfully fused to the syringe body 10, optionally a further thermal post-treatment may follow, which is however not illustrated in the figures. This thermal post-treatment serves to relax potentially still existing residual stresses in the syringe body/needle assembly 1. In the embodiment described above, the syringe body 10 has an average thermal expansion coefficient $\alpha_{(20-300)}$ of $4.9 \times 10^{-6}$/K, but the needle 20 has an average thermal expansion coefficient from $10 \times 10^{-6}$/K to $20 \times 10^{-6}$/K. Due to these differences, stresses may arise which are at least considerably reduced by such a thermal post-treatment, and are at least brought below the critical level for the use as a syringe.

Furthermore, advantageously, the thermal expansion coefficient of the first material of the connecting body may be between that of the second material of the syringe body 10 and that of the needle 20 material. In this case, the first material of the connecting body 30 then has an conciliating effect on the arising stresses.

Instead of the short wave IR radiation 41 it is also possible to use an Nd:YAG laser 41 for fusing the connecting body 30 at least partially. The arrangement of syringe body 10, connecting body 30, and needle 20 corresponds to what has been described above. The materials used and the dimensions are also identical. The arranged system consisting of syringe body 10, needle 20, and sintered body 30 is rotated at a rotational speed from 1 to 120 U/min, preferably from 1 to 60 U/min, and more preferably from 1 to 30 U/min, yet even more preferably from 1 to 10 U/min. At the height of the sintered body 30, the sintered body 30 is irradiated radially from the outside using a laser beam of a wavelength between 800 nm and 1500 nm, preferably from 900 to 1100 nm. A scanner or other suitable device is used to expand the beam so that a laser line is formed having a length of about 0.05 to 12 mm, or for example a length that covers at least the height of the connecting body 30. The laser power is set such that the connecting body 30, or sintered body 30 in this case, fuses within 1 to 60 seconds, preferably within 1 to 30 seconds, and more preferably within 1 to 10 seconds, to hermetically bond and seal the nozzle 11 to the needle 20. During irradiation of laser 41, a conventional auxiliary heater or infrared heater or other suitable heating means 45 heats the entire system to several hundred degrees Celsius, at least to the extent that any excessive stresses in the syringe body 10 or in the nozzle 11 due to the laser irradiation 41 are prevented from arising. For example, a conventional auxiliary heater 45 with, e.g., 500 W of electric power may be used.

The successful fusion between needle 20 and syringe body 10 may be followed by a thermal post-treatment, in order to remove residual stresses from the syringe body/needle assembly 1 or at least to considerably reduce them.

According to another preferred embodiment of the invention, local heating of the connecting body 30 may be accomplished using microwave irradiation 41. The arrangement of syringe body 10, connecting body 30, and needle 20 corresponds to the above described. The materials used, with the exception of the connecting body 30, and the dimensions of the components are also identical. As a connecting body 30, a sintered body of Fiolax® clear is used, which is mixed with 1 to 95% of iron powder. The system consisting of syringe body 10, needle 20 and sintered body 30 is placed in a cylindrical microwave resonator having an inner diameter of, e.g., 30 mm, and is rotated synchronously with a rotational speed between 1 and 120 U/min. Through a microwave waveguide 40, microwave radiation 41 of a frequency between 0.8 GHz and 30 GHz, preferably between 0.85 and 3 GHz, is coupled into the microwave resonator.

The microwave power may be adjusted, by pulsing or other appropriate control measures, such that the sintered body 30 fuses within a period from 1 to 60 seconds, preferably within 1 to 30 seconds, and more preferably within 1 to 10 seconds, to hermetically bond and seal the syringe body 10 to the needle 20.

During microwave irradiation 41, advantageously, a stream of hot air 46 at a temperature from 30° C. to 800° C., in the present case for example 600° C., or another suitable heating means 45 heats the entire system which comprises at least the syringe body 10 and the nozzle 11 to several hundred degrees Celsius, and at least to the extent that any impermissible excessive stresses in the syringe body 10 or in the nozzle 11 due to the microwave irradiation 41 are prevented from arising. This may be achieved, for example, by heating the entire system at least to the strain point thereof. After the needle 20 has been fused with the syringe body 10 or nozzle 11, a thermal post-treatment as described above may follow to relax stresses possibly still existing in the assembled syringe.

Figure 2:
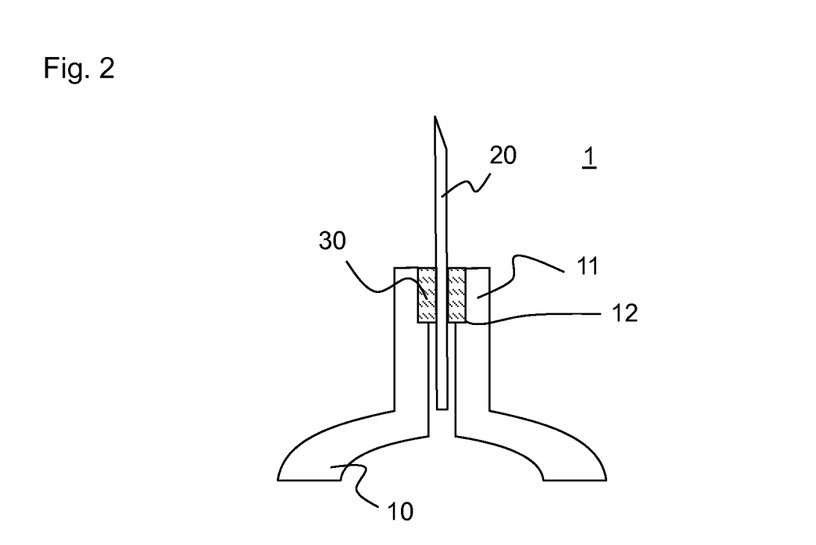
FIG. 2 shows the connecting body arranged distally in a distally oriented recess in the nozzle, the connecting body only filling parts of the nozzle.

Advantageously, prior to the microwave irradiation, the system of syringe body and connecting body is heated to a temperature which promotes the absorption of microwave radiation. Generally, different geometric arrangements of nozzle 11 and connecting member 30 are conceivable. FIG. 2 illustrates an embodiment in which nozzle 11 has a distally oriented recess 12, so that a tube-shaped connecting member 30 may be inserted from the free end of the nozzle, i.e. from a distal direction. Recess 12 is dimensioned such that the connecting body 30 in its installed state substantially flushes with the distal edge of nozzle 11, without however filling the entire extent of nozzle 11. Recesses 12 may be of advantage for the stability of the syringe body/needle assembly 1 in serving as an abutment for the connecting body 30. Also, during manufacturing of the syringe body/needle assembly 1 they allow for automatic centering or automatic proper placement of the connecting body 30 in the nozzle 11.

Figure 3:
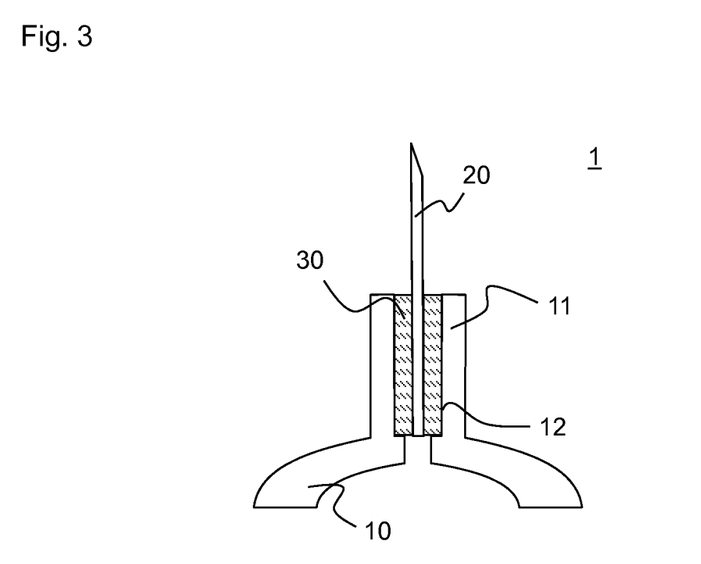
FIG. 3 shows the connecting body arranged distally in a distally oriented recess in the nozzle.

FIG. 3 illustrates an arrangement of the connecting body 30 in the nozzle 11 in a distally oriented recess 12, wherein substantially the entire nozzle 11 is filled by connecting body 30. This may be advantageous to avoid so called dead space, i.e. for example drug amounts that are non-injectable due to the syringe geometry.

Figure 4:
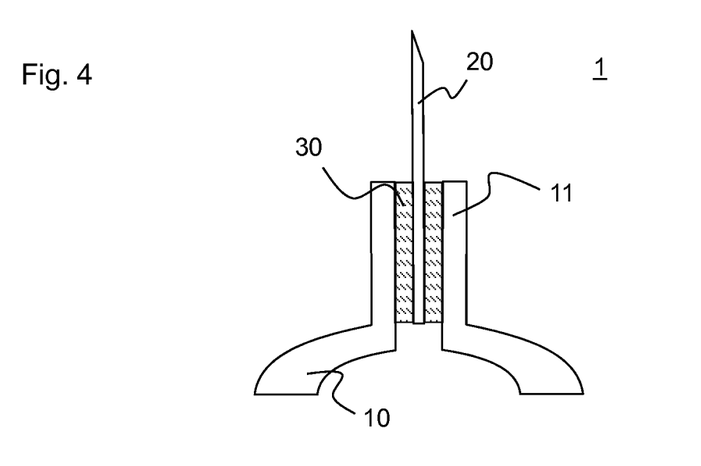
FIG. 4 shows the connecting body arranged in the nozzle without a recess.

FIG. 4, in contrast, illustrates an arrangement of the connecting body 30 in nozzle 11 which dispenses with a recess in the nozzle.

Figure 5:
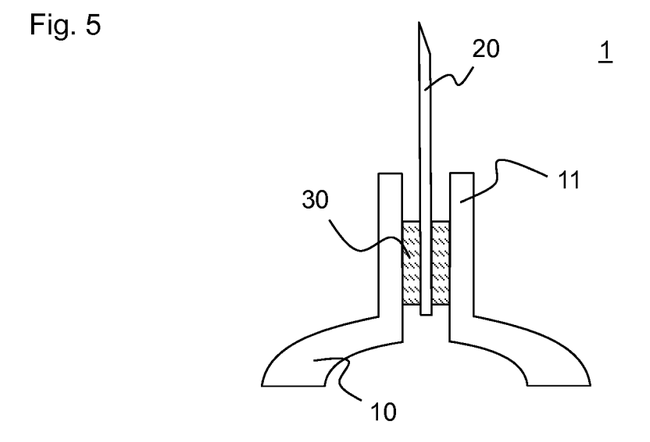
FIG. 5 shows the connecting body arranged in the center of the nozzle without recess.

FIG. 5 shows the connecting body 30 arranged in the center of nozzle 11 without any recess.

Figure 6:
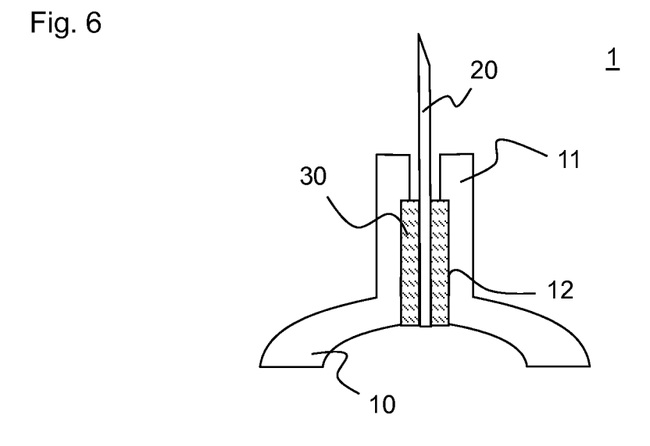
FIG. 6 shows the connecting body arranged proximally in a proximally oriented recess in the nozzle.

A proximal arrangement of the connecting body 30 in a proximally oriented recess 12 in nozzle 11 is illustrated in FIG. 6. In this case, connecting body 30 may be inserted into the recess 12 in nozzle 11 from the inside of the syringe body.

Figure 7:
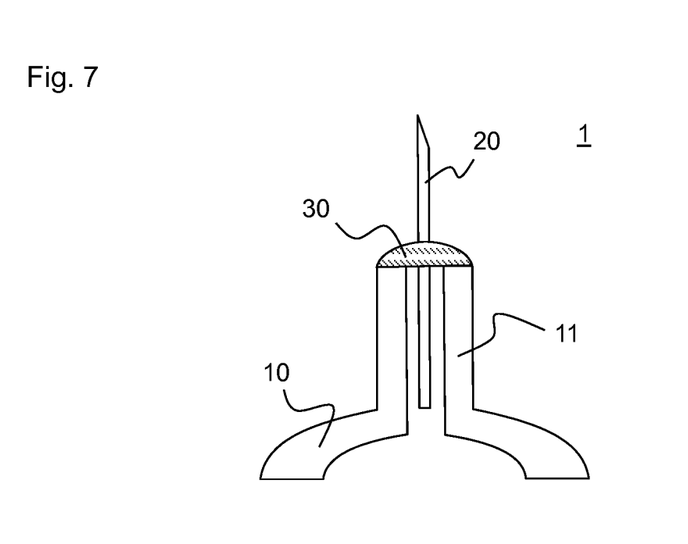
FIG. 7 shows the connecting body placed at the distal end of the nozzle.
Figure 8:
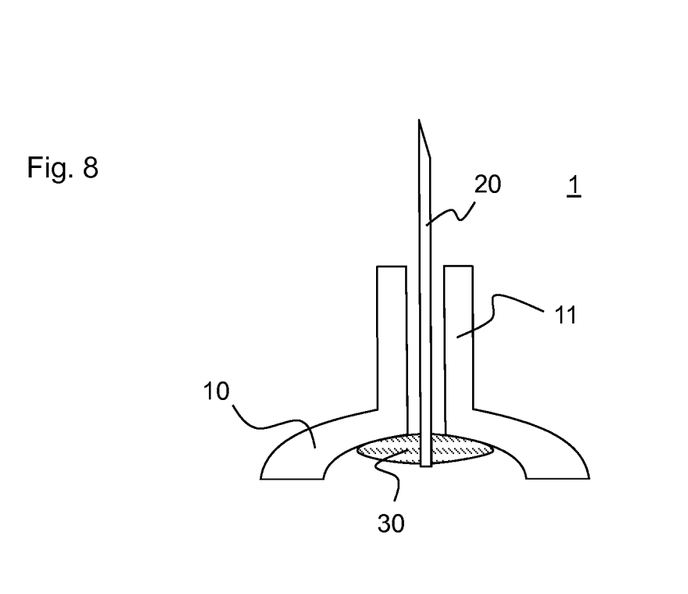
FIG. 8 shows the connecting body placed at the proximal end of the nozzle.

The embodiments of FIGS. 7 and 8 illustrate an arrangement in which the connecting body 30 is not placed in nozzle 11 but at nozzle 11. In FIG. 7, connecting body 30 is placed on the distal edge of the nozzle. In FIG. 8, connecting body 30 is placed proximally to nozzle 11 and therefore faces the interior of the syringe.

Figure 9:
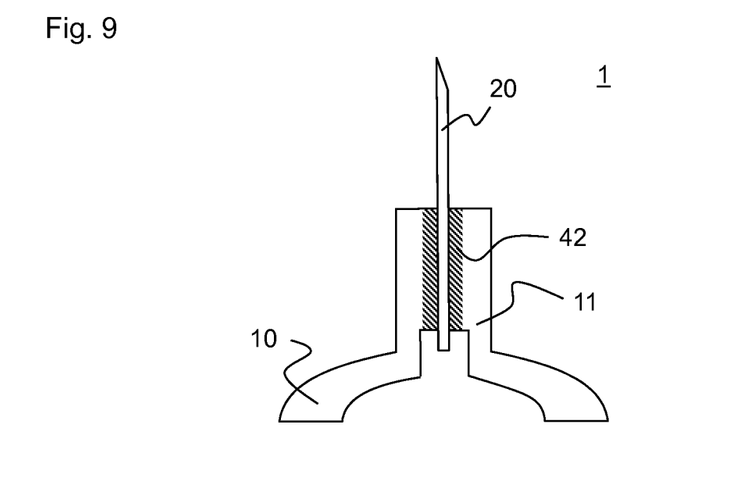
FIG. 9 shows a schematic cross section through a syringe body/needle assembly without connecting body.

FIG. 9 shows a schematic cross section through a syringe body/needle assembly 1, in which an additional connecting body 30 has been dispensed with. This embodiment can be obtained by chemically or structurally modifying the inner surface of nozzle 11, so that these areas 42 exhibit an increased radiation absorption over unmodified syringe parts 11. For example, a suitable surface treatment may cause radiation active ions to diffuse into the surface region of the inner nozzle channel, which leads to a local increase in radiation absorption in the ion diffusion regions.

Figure 10:
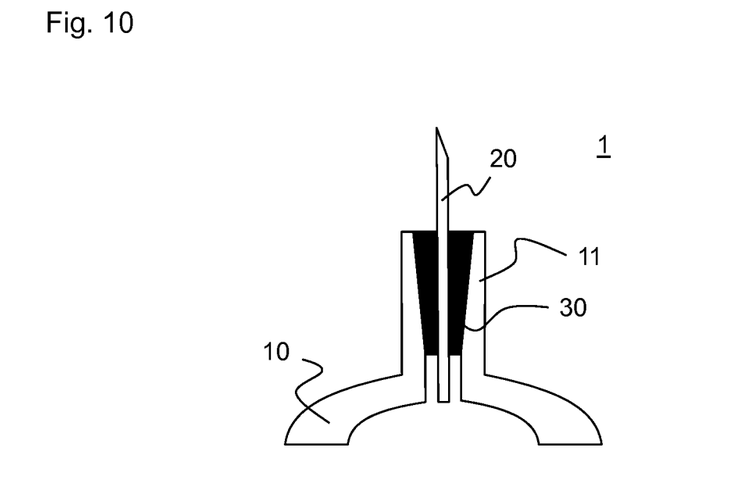
FIG. 10 shows a schematic cross section through a syringe body/needle assembly including a conical connecting body.

FIG. 10 shows a schematic cross section through a syringe body/needle assembly 1. In this case, the connecting body 30 has a conical shape. An advantage thereof is that the connecting body 30 centers itself during assembly and contacting engagement thereof all around is ensured.

Figure 11:
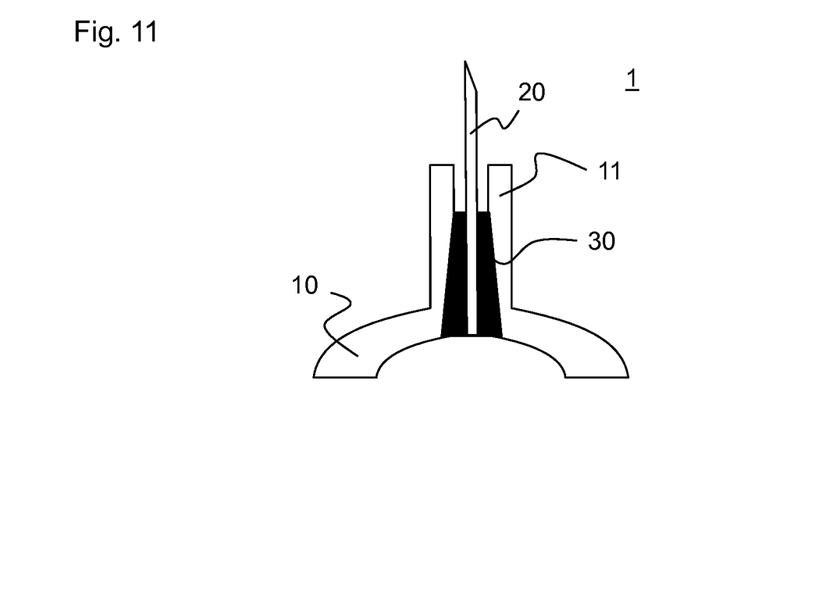
FIG. 11 shows a schematic cross section through a syringe body/needle assembly with a conical connecting body in an orientation different to that of FIG. 10.

FIG. 11 shows the same configuration as in FIG. 10, but with the connecting body 30 in a different orientation. Here, the cross-section thereof tapers in the direction of the needle tip.

Figure 12:
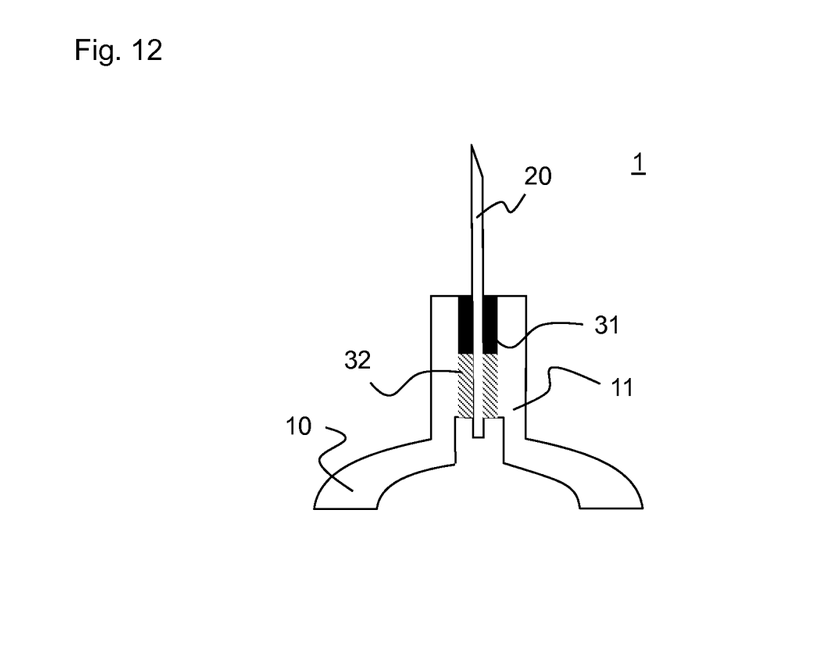
FIG. 12 shows a schematic cross section through a syringe body/needle assembly including a connecting body that consists of two different glasses.

FIG. 12 shows a schematic cross section through a syringe body/needle assembly 1. Here, the connecting body 30 consists of two different glasses 31, 32. For being clearly marked, the glasses may be colored differently. Furthermore, glass 31 may have a lower melting temperature than glass 32. This may be beneficially used, since glasses with a low melting point (for example, to protect the needle) often have the disadvantage of a lower chemical stability. The chemically more stable glass prevents a contact with the drug. If, however, glass 31 has a higher melting point than glass 32, this provides the advantage that glass 32 does not completely melt and thus does not come into contact with the needle. Therefore, the needle is not heated so much in this region and retains its bending strength. The transition region to the molten glass 32 is mechanically protected by connecting bodies 31. In this way, the bending strength of the needle as a whole is enhanced.

What is claimed is:

1. A syringe body and needle assembly, comprising:
   a syringe body having a nozzle that has an opening;
   a needle fixed to a region of the syringe body or the nozzle of the syringe body so that the needle extends from the opening of the nozzle and in communication with an interior of the syringe body; and
   a connecting body hermetically sealing the needle to the region, the connecting body comprising a first material provided in the region, the first material absorbing more electromagnetic radiation within a wavelength range than a second material from which the syringe body is made of, wherein the needle is fused into the first material which absorbs more electromagnetic radiation, wherein, in the wavelength range of the electromagnetic radiation, the first material has a total energy absorption in a single pass of the radiation that is at least 10% A higher than that of the second material of the syringe body, and wherein the connecting body comprises doped glass.

2. The assembly as claimed in claim 1, wherein the total energy absorption is at least 30% higher.

3. The assembly as claimed in claim 1, wherein the total energy absorption is at least 50% higher.

4. The assembly as claimed in claim 1, wherein the doped glass comprises a component that absorbs the electromagnetic radiation.

5. The assembly as claimed in claim 1, wherein the first material comprises glass doped with compounds selected from the group consisting of chromium, nickel, copper, iron, cobalt, rare earths, and elements or compounds absorbing in the wavelength range of the electromagnetic radiation.

6. The assembly as claimed in claim 1, wherein the second material is glass.

7. The assembly as claimed in claim 1, wherein the wavelength range is from 800 to 3000 nanometers.

8. The assembly as claimed in claim 1, wherein the wavelength range is from 800 to 1500 nanometers.

9. The assembly as claimed in claim 1, further comprising more than one connecting body.

10. The assembly as claimed in claim 1, wherein the connecting body comprises a first connecting body in an upper region of the nozzle and a second connecting body in a lower region of the nozzle.

11. The assembly as claimed in claim 1, wherein both the syringe body and the connecting body are made of glass, and wherein the glass of the connecting body is chemically and/or structurally different from the glass of the syringe body.

12. The assembly as claimed in claim 1, wherein the region is in at least one of an upper end, a lower end or in a center of the nozzle.

13. The assembly as claimed in claim 1, wherein the region is a recess in the nozzle, which opens to at least one side.

14. The assembly as claimed in claim 1, wherein the second material comprises plastic material.

15. A syringe body with needle assembly, comprising:
a syringe body having a nozzle that has an opening;
a connecting body comprising a first material that absorbs more electromagnetic radiation than a second material of the syringe body, wherein the first material of the connecting body comprises doped glass material; and
a needle fixed in the opening of the nozzle, the needle being hermetically sealed by the connecting body to a region of the nozzle or to an interior of the syringe body with the needle fused in the first material.

16. The assembly as claimed in claim 15, wherein the region is in the nozzle.

17. The assembly as claimed in claim 16, wherein the connecting body is fitted into a recess in the nozzle which opens to at least one side.

18. The assembly as claimed in claim 15, wherein the second material of the syringe body comprises glass material or plastic material.

19. The assembly as claimed in claim 15, wherein the region is in the interior of the syringe body.

* * * * *